US008957188B2

(12) United States Patent
Gildersleeve et al.

(10) Patent No.: US 8,957,188 B2
(45) Date of Patent: Feb. 17, 2015

(54) ANTIBODIES THAT BIND GALNAC1-3GAL, PHARMACEUTICAL COMPOSITIONS AND METHODS OF USING SAME

(75) Inventors: Jeffrey Gildersleeve, Frederick, MD (US); Zhitao Li, Vestal, NY (US); Qian Li, Timonium, MD (US); Miriam Anver, Rectortown, VA (US); Donna O. Butcher, Kearneysville, WV (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 674 days.

(21) Appl. No.: 12/752,331

(22) Filed: Apr. 1, 2010

(65) Prior Publication Data

US 2010/0254898 A1    Oct. 7, 2010

Related U.S. Application Data

(60) Provisional application No. 61/165,675, filed on Apr. 1, 2009.

(51) Int. Cl.
| | |
|---|---|
| *C07K 16/00* | (2006.01) |
| *C07K 16/30* | (2006.01) |
| *A61K 51/10* | (2006.01) |
| *G01N 33/534* | (2006.01) |

(52) U.S. Cl.
CPC ............. *A61K 51/1045* (2013.01); *C07K 16/00* (2013.01); *C07K 16/30* (2013.01); *C07K 16/3092* (2013.01); *G01N 33/534* (2013.01); *G01N 2400/02* (2013.01)
USPC .................... 530/387.5; 530/388.1; 530/391.1

(58) Field of Classification Search
CPC ................................ C07K 16/30; C07K 16/00
USPC ........................ 435/7.1, 7.23, 188; 424/1.49; 530/387.5, 388.1, 391.1, 391.3
See application file for complete search history.

(56) References Cited

U.S. PATENT DOCUMENTS

| | | | |
|---|---|---|---|
| 4,839,290 A | 6/1989 | Kaieda et al. | |
| 5,229,289 A | 7/1993 | Kjeldsen et al. | |
| 5,242,799 A | 9/1993 | Samuel et al. | |
| 2007/0059769 A1* | 3/2007 | Blixt et al. | 435/7.1 |
| 2010/0104572 A1* | 4/2010 | Luria | 424/137.1 |

OTHER PUBLICATIONS

Li et al. (Int. J. Cancer, 2010, 126: 459-468).*
Carrilho et al., *Virchows Arch.*, 437, 173-179 (2000).
Chihara et al., *Lab. Investigation*, 85 (7), 895-907 (2005).
De Paz et al., *QSAR Comb. Sci.*, 25 (11), 1027-1032 (2006).
Dube et al., *Nat. Rev. Drug Discovery*, 4 (6), 477-488 (2005).
Freire et al., *Mini Rev. Med. Chem.*, 6 (12), 1357-1373 (2006).
Fuster et al., *Nat. Rev. Cancer*, 5 (7), 526-542 (2005).
Gildersleeve et al., *Bioconjugate Chem.*, 19 (7), 1485-1490 (2008).
Hamada et al., *Cancer Lett.*, 74 (3), 167-173 (1993).
Hammarström et al., *Biochem.*, 16 (12), 2750-2755 (1977).
Hirao et al., *Cancer*, 72 (1), 154-159 (1993).
Hsu et al., *Mol. BioSyst.*, 4 (6), 654-662 (2008).
Imberty et al., *Glycoconj. J.*, 11 (5), 400-413 (1994).
Jordanova et al., *Clin. Cancer Res.*, 14 (7), 2028-2035 (2008).
Li et al., *Mol. Cancer Ther.*, 8 (4), 971-979 (2009).
Liang et al., *Curr. Opin. Chem. Biol.*, 12 (1), 86-92 (2008).
Manimala et al., *Angew. Chem. Int. Ed. Engl.*, 45, 3607-3610 (2006).
Manimala et al., *ChemBioChem*, 6 (12), 2229-2241 (2005).
Manimala et al., *Glycobiology*, 17 (8), 17C-23C (2007).
Oyelaran et al., *Expert Rev. Vaccines*, 6 (6), 957-969 (2007).
Oyelaran et al., *Glycobiology*, Poster No. 55 (2008 ).
Paulson et al., *Nat. Chem. Biol.*, 2 (5), 238-248 (2006).
Podolsky et al., *J. Biol. Chem.*, 260 (14), 8262-8271 (1985).
Reese et al., *Cancer Research*, 52, 5235-5243 (1992).
Siddiqui et al., *J. Biol. Chem.*, 253 (7), 2168-2175 (1978).
Spieker-Polet et al., *Proc. Natl. Acad. Sci. USA*, 92 (20), 9348-9352 (1995).
Springer et al., *Cancer Detect. Prev.*, 19 (4), 374-380 (1995).
Terasawa et al., *Cancer Res.*, 56 (9), 2229-2232 (1996).
Van Vliet et al., *Int. Immunol.*, 17 (5), 661-669 (2005).
Van Vliet et al., *Trends Immunol.*, 29 (2), 83-90 (2008).
Yeasmin et al., *Clin. Cancer Res.*, 14 (6), 1686-1691 (2008).
Yokota et al., *Cancer Res.*, 41 (10), 4185-4190 (1981).
Young et al., *Gyn. Oncol.*, 109 (1), 140-145 (2008).

* cited by examiner

*Primary Examiner* — Mark Halvorson
*Assistant Examiner* — Yan Xiao
(74) *Attorney, Agent, or Firm* — Leydig, Voit & Mayer, Ltd.

(57) ABSTRACT

Monoclonal antibodies to carbohydrate antigens containing a terminal GalNAcα1-3Gal are provided. The antibodies of the present invention are found to specifically recognize GalNAcα1-3Gal with little cross-reactivity to other structurally similar antigens such as GalNAcα1-6Gal, blood group A, Forssman antigen and the Tn antigen on both solution assays and human tissue. Compositions comprising the monoclonal antibodies, as well as methods of diagnosis, treatment and prognostication are also provided.

20 Claims, 7 Drawing Sheets

ANTIBODIES THAT BIND GALNAC1-3GAL, PHARMACEUTICAL COMPOSITIONS AND METHODS OF USING SAME

CROSS-REFERENCE TO RELATED APPLICATION

This application claims the benefit of U.S. Provisional Application No. 61/165,675, filed Apr. 1, 2009, the entire contents of which are incorporated herein by reference.

BACKGROUND OF THE INVENTION

Major changes occur in carbohydrate expression during the onset and progression of cancer. These changes include both loss of normal cell surface carbohydrates (e.g., ABO blood group antigens) as well as greater levels of expression of carbohydrate structures that normally have lesser and/or restricted expression levels in most healthy adults (called tumor-associated carbohydrate antigens). In many cases, these tumor associated antigens are found on cell surfaces and/or secreted proteins, making them accessible for binding and detection. As a result, carbohydrate antigens have become important molecular targets for cancer diagnostics and therapeutics. One example is the Tn antigen; a carbohydrate composed of a GalNAc residue alpha linked to either a serine or threonine residue of a polypeptide/protein.

Studies have examined the expression of the Tn antigen in cervical and other cancers, and evaluated its utility as a prognostic marker; however, the results remain a subject of considerable debate. These studies have relied on immunohistochemical staining or Western blotting with Tn binding antibodies and/or lectins for the detection of the Tn antigen.

BRIEF SUMMARY OF THE INVENTION

In an embodiment, the invention provides a monoclonal antibody, or binding fragment thereof, which binds specifically to GalNAcα1-3Gal.

In some embodiments the antibody or fragment thereof is labeled with a detectable moiety, such as a fluorophore, or radionuclide, or a chemiluminescent agent, or a bioluminescent agent or an enzyme.

In an embodiment, the present invention also provides a monoclonal antibody, or binding fragment thereof which binds specifically to GalNAcα1-3Gal, and is bound to a solid matrix.

In another embodiment, the invention provides a pharmaceutical composition comprising a monoclonal antibody or binding fragment thereof, which binds specifically to GalNAcα1-3Gal, and including one or more of a pharmaceutically acceptable carrier, excipient, or diluent or a second therapeutic agent, or combinations thereof.

In another embodiment, the invention provides a hybridoma cell line which produces a monoclonal antibody which binds specifically to GalNAcα1-3Gal. In one embodiment, the hybridoma cell line is the 132-3 cell line. In another embodiment, the hybridoma cell line is the 74-3 cell line.

In an embodiment, the present invention additionally provides a method of detecting the presence of cancer or precancer in a subject comprising: contacting a labeled monoclonal antibody or binding fragment thereof, which binds specifically to GalNAcα1-3Gal, with a biological sample taken from the subject under conditions allowing for a complex to form between the monoclonal antibody or binding fragment thereof, and the sample; detecting the complex; and comparing the amount of monoclonal antibody or binding fragment thereof in the test sample with an amount of monoclonal antibody or binding fragment thereof from a known normal biological sample, wherein an increased amount of monoclonal antibody binding in the test sample is indicative of cancer or precancer.

In an embodiment, the invention provides a method of treating or inhibiting cancer in a subject comprising administering to the subject the pharmaceutical composition comprising a monoclonal antibody or binding fragment thereof, which binds specifically to GalNAcα1-3Gal, in an amount that is effective to treat or inhibit cancer in the subject.

In yet another embodiment, the invention provides a method for radioimaging a cancer cell or tumor in a subject which comprises: administering to the subject a composition comprising a monoclonal antibody, or binding fragment thereof, which binds specifically to GalNAcα1-3Gal, and is labeled with a radioisotope; detecting the radiation emitted from the composition in the subject; and forming a high contrast image therefrom.

In still another embodiment, the invention provides a method of predicting the survival of a subject having cancer comprising: contacting a labeled monoclonal antibody or binding fragment thereof, which binds specifically to GalNAcα1-3Gal, with a biological sample taken from the subject under conditions allowing for a complex to form between the monoclonal antibody or binding fragment thereof, and the sample; detecting the complex; and determining the amount of monoclonal antibody or binding fragment thereof bound in the sample, and correlating the amount of monoclonal antibody or binding fragment to survival of the subject.

BRIEF DESCRIPTION OF THE SEVERAL VIEWS OF THE DRAWING(S)

FIG. 1 is a depiction of the chemical structures of GalNAcα1-3Gal and structurally similar carbohydrate antigens.

FIGS. 2A-2D are graphs showing the microarray profiling of 132-3 antibody. The selected antigens (mostly structurally related) are present on the array. FIG. 2A shows the microarray profiling of monoclonal antibodies to Dolichos biflorus agglutinin (DBA). FIG. 2B shows the microarray profiling of the monoclonal antibody 132-2 of the present invention (specific for GalNAcα1-3Gal). FIG. 2C shows the microarray profiling of monoclonal antibodies to 12-1 (specific for GalNAcα1-6Gal). FIG. 2D shows the microarray profiling of monoclonal antibodies to 81FR2.2 (specific for blood group A antigens). The dilution of reagents are DBA (0.5 μg/mL); 132-3 (1:10); 12-1 (1:50); 81FR2.2 (1:1000).

DETAILED DESCRIPTION OF THE INVENTION

Figure 1:
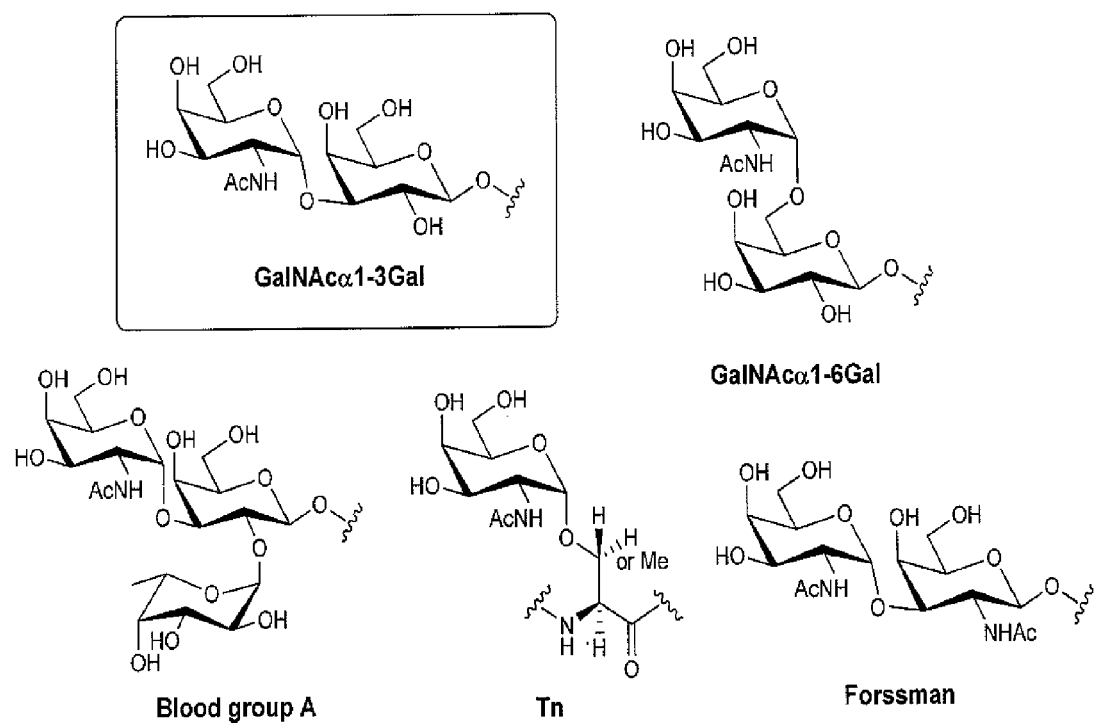
Figure 2A:
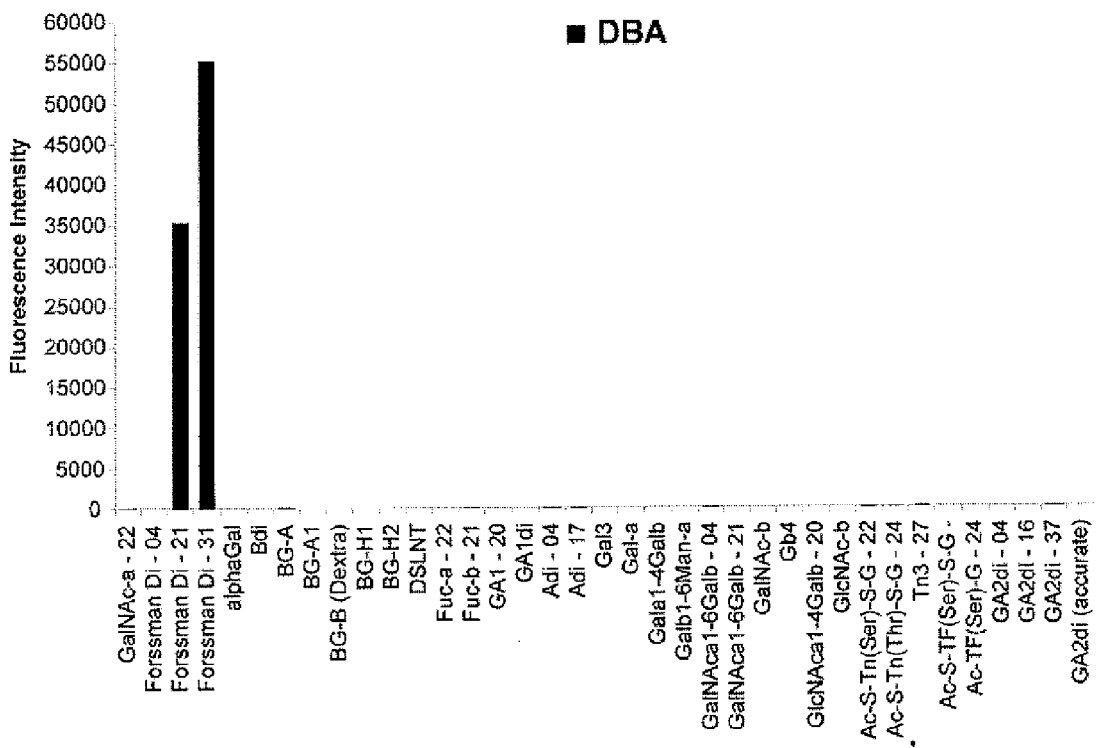
Figure 2B:
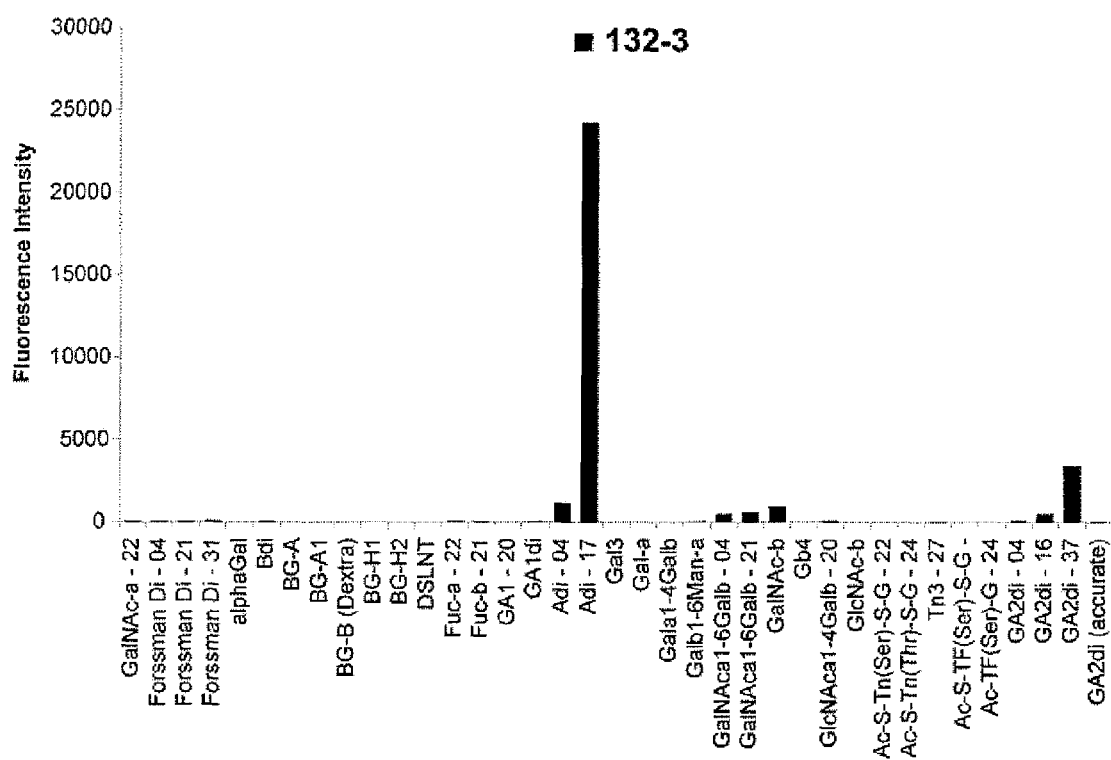
Figure 2C:
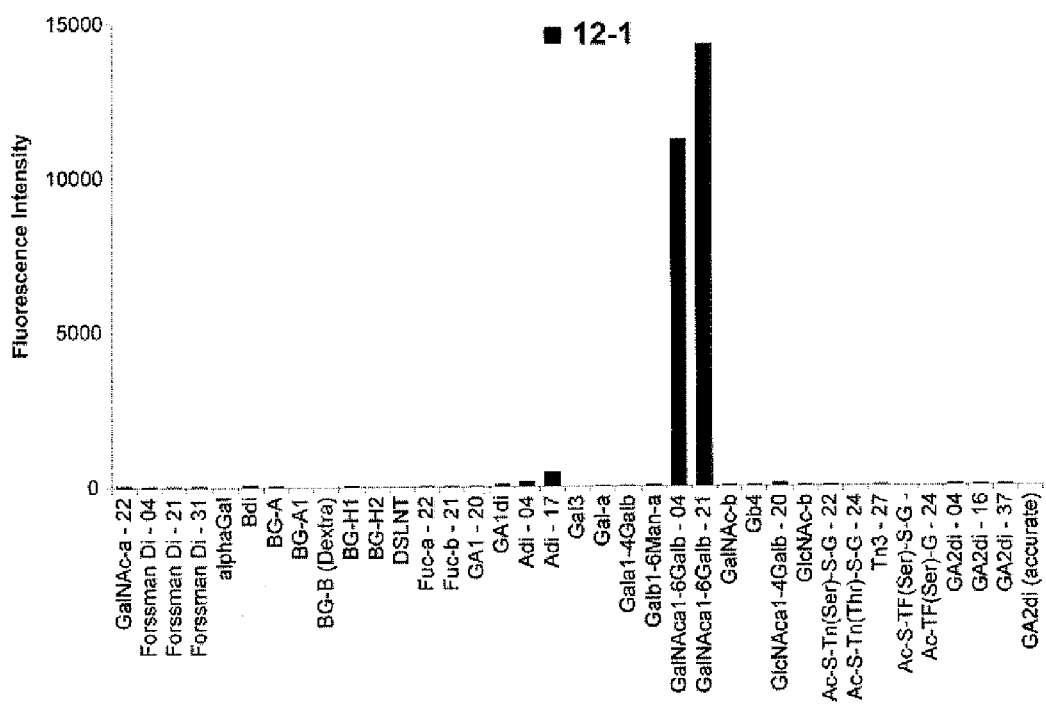
Figure 2D:
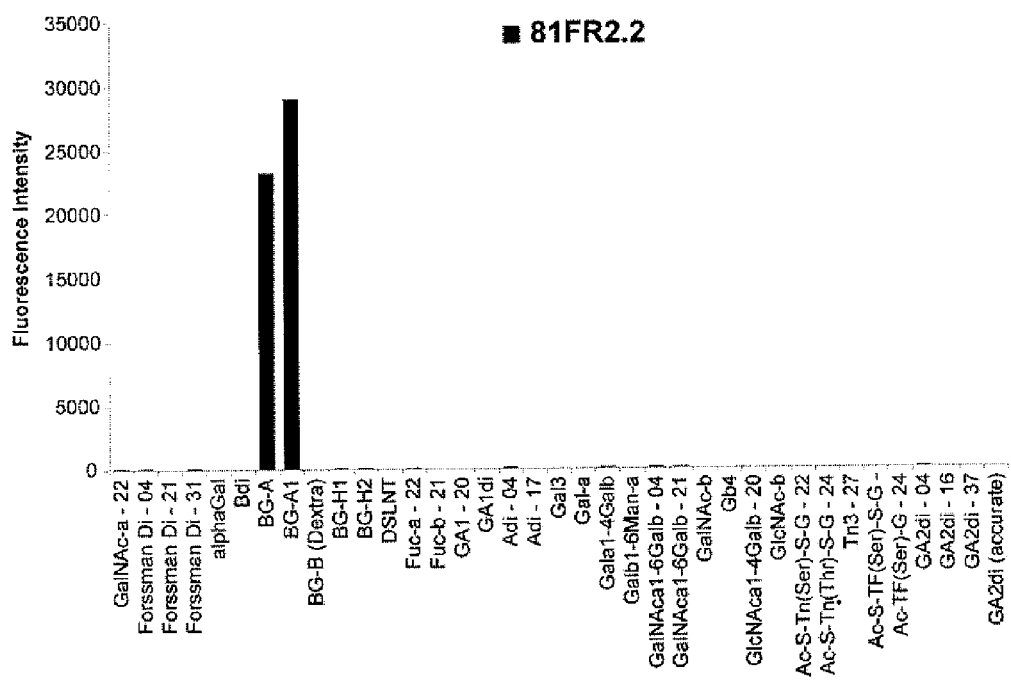

In an embodiment, the invention provides a monoclonal antibody, or binding fragment thereof, which binds specifically to GalNAcα1-3Gal.

In some embodiments the antibody or fragment thereof is labeled with a detectable moiety, such as a fluorophore, or radionuclide, or a chemiluminescent agent, or a bioluminescent agent or an enzyme.

In an embodiment, the present invention also provides a monoclonal antibody, or binding fragment thereof which binds specifically to GalNAcα1-3Gal, and is bound to a solid matrix.

In another embodiment, the invention provides a pharmaceutical composition comprising a monoclonal antibody or binding fragment thereof, which binds specifically to GalNAcα1-3Gal, and including one or more of a pharmaceutically acceptable carrier, excipient, or diluent or a second therapeutic agent, or combinations thereof. In an embodiment, the pharmaceutical composition includes a therapeutic agent selected from the group consisting of: drugs, radioisotopes, immunomodulators, lectins, toxins, and combinations thereof. In another embodiment, the present invention provides a pharmaceutical composition comprising the monoclonal antibody, or binding fragment thereof, according to the invention, and a pharmaceutically acceptable carrier, excipient, or diluent.

In an embodiment, a kit is provided, comprising reagents in separate containers, at least one of the reagents in a container being a composition comprising a monoclonal antibody or binding fragment thereof, which binds specifically to GalNAcα1-3Gal, and including one or more of a pharmaceutically acceptable carrier, excipient, or diluent and/or a second therapeutic agent, or combinations thereof.

In an embodiment, the present invention additionally provides a method of detecting the presence of cancer or precancer in a subject comprising: contacting a labeled monoclonal antibody or binding fragment thereof, which binds specifically to GalNAcα1-3Gal, with a biological sample taken from the subject under conditions allowing for a complex to form between the monoclonal antibody or binding fragment thereof, and the sample; detecting the complex; and comparing the amount of monoclonal antibody or binding fragment thereof in the test sample with an amount of monoclonal antibody or binding fragment thereof from a known normal biological sample, wherein an increased amount of monoclonal antibody binding in the test sample is indicative of cancer or precancer. In an embodiment, the cancer or precancer is found in tissues or cells selected from the group consisting of: skin and squamous cells, cervix, esophagus, larynx, oral, nasopharyngeal, salivary gland, stomach, colon, rectum, liver, bile duct, pancreas, lung, bone, soft tissue, melanoma, breast, ovarian, prostate, penis, testis, urinary tract, bladder, kidney, brain, thyroid, adrenal, thymus, endocrine pancreas, eye, and combinations thereof.

In an embodiment, the invention provides a method of treating or inhibiting cancer in a subject comprising administering to the subject the pharmaceutical composition comprising a monoclonal antibody or binding fragment thereof, which binds specifically to GalNAcα1-3Gal, in an amount that is effective to treat or inhibit cancer in the subject.

In an embodiment, the invention provides a method for radioimaging a cancer cell or tumor in a subject which comprises: administering to the subject a composition comprising a monoclonal antibody, or binding fragment thereof, which binds specifically to GalNAcα1-3Gal, and is labeled with a radioisotope; detecting the radiation emitted from the composition in the subject; and forming a high contrast image therefrom.

In an embodiment, the invention provides a method of predicting the survival of a subject having cancer comprising: contacting a labeled monoclonal antibody or binding fragment thereof, which binds specifically to GalNAcα1-3Gal, with a biological sample taken from the subject under conditions allowing for a complex to form between the monoclonal antibody or binding fragment thereof, and the sample; detecting the complex; and determining the amount of monoclonal antibody or binding fragment thereof bound in the sample, and correlating the amount of monoclonal antibody or binding fragment to survival of the subject.

In accordance with the present invention, monoclonal antibodies were generated that specifically bind GalNAcα1-3Gal. Antibody specificity was verified by a combination of carbohydrate microarray profiling, dot blotting, and immunohistochemical staining. The antibodies were then used to evaluate antigen expression in various human tissues. It was found that GalNAcα1-3Gal was expressed at high levels in certain squamous carcinomas of the cervix, larynx, and in other tissues as described above. More importantly, the expression of GalNAcα1-3Gal had a statistically significant correlation with 5 year survival rates, indicating that it is a biochemical marker for prognosticating survival in many cancers, including, for example, cervical cancer and laryngeal cancer and can be useful in making treatment decisions.

The term "cancer antigen", or "cancer specific antigen" as used herein, refers to any molecule (e.g., protein, peptide, lipid, carbohydrate, etc.) solely or predominantly expressed or over-expressed by a tumor cell or cancer cell, such that the antigen is associated with the presence of a tumor or cancer. The cancer antigen can additionally be expressed by normal, non-tumor, or non-cancerous cells. However, in such cases, the expression of the cancer antigen by normal, non-tumor, or non-cancerous cells is not as robust as the expression by tumor or cancer cells. In this regard, the tumor or cancer cells can over-express the antigen, or express the antigen at a significantly higher level, as compared to the expression of the antigen by normal, non-tumor, or non-cancerous cells. Also, the cancer antigen can additionally be expressed by cells of a different state of development or maturation. For instance, the cancer antigen can be additionally expressed by cells of the embryonic or fetal stage, in which cells are not normally found in an adult host. Alternatively, the cancer antigen can be additionally expressed by stem cells or precursor cells, which are cells that are not normally found in an adult host.

The term "naturally occurring" as used herein means an endogenous or exogenous protein isolated and purified from animal tissue or cells.

The term "isolated and purified" as used herein means a protein that is essentially free of association with other proteins or polypeptides, e.g., as a naturally occurring protein that has been separated from cellular and other contaminants by the use of antibodies or other methods of as a purification product of a recombinant host cell culture.

The term "biologically active" as used herein means an enzyme or protein having structural, regulatory, or biochemical functions of a naturally occurring molecule.

Nonlimiting examples of antibody fragments or antigen bindable fragments, as herein defined, include those that bind to epitopes on the GalNAcα1-3Gal antigen, for example: Fab fragments, F(ab)$_2$ fragments, Fab' fragments, fragments produced by F(ab) expression libraries, F(ab')$_2$ fragments, Fd fragments, Fd' fragments and Fv fragments. The antibodies may be human, or from animals other than humans, preferably mammals, such as rat, mouse, guinea pig, rabbit, goat, sheep, and pig. In an embodiment, the antibodies are mouse monoclonal antibodies and antigen-binding fragments or portions thereof. In addition, chimeric antibodies and hybrid antibodies are embraced by the present invention.

In accordance with the present invention, the monoclonal antibodies and binding fragments thereof may be characterized as those which are: 1) produced from a hybridoma cell line, for example, the hybridoma cell line 74-3 or 132-3; 2)

antibodies that are capable of binding to the same antigenic determinant of GalNAcα1-3Gal, as does the monoclonal antibody produced by the hybridoma cell lines of (1); 3) binding fragments of the monoclonal antibody produced by the hybridoma cell lines; or 4) binding fragments of a monoclonal antibody capable of binding to the same antigenic determinant of GalNAcα1-3Gal, as does the monoclonal antibody produced by the hybridoma cell lines.

In an embodiment, the monoclonal antibody of the present invention can be obtained by culturing a hybridoma producing the antibody of the present invention in a culture medium, for example, in RPMI1640 medium that contains fetal bovine serum. Alternatively, it can be obtained by, for example, preparing a gene comprising a heavy chain or a light chain, in which a DNA encoding a constant region of heavy chain or light chain is ligated to a DNA encoding each variable region by means of a PCR method or a chemical synthesis; inserting the obtained gene into a conventionally-used expression vector (e.g., pcDNA3.1 (Invitrogen, Carlsbad, Calif.) capable of expressing the gene; expressing the gene in a host cell such as a CHO cell (Chinese hamster ovary cell) or *Escherichia coli* to produce the antibody; and purifying the obtained antibody from the culture medium using a Protein A/G column or the like.

Furthermore, the monoclonal antibody of the present invention may be obtained by, for example: preparing a hybridoma from an animal immunized with GalNAcα1-3Gal; culturing the hybridoma; and selecting a monoclonal antibody which can bind to a surface of living cancer cells from the obtained monoclonal antibodies. Examples of such a monoclonal antibody include those produced from hybridoma cell lines 74-3 or 132-3.

Included in the scope of the present invention are conjugates, e.g., bioconjugates, comprising any of the inventive monoclonal antibodies (including any of the functional portions or variants thereof), host cells, populations of host cells, or antibodies, or antigen binding portions thereof. Conjugates, as well as methods of synthesizing conjugates in general, are known in the art (See, for instance, Hudecz, F., *Methods Mol. Biol.*, 298: 209-223 (2005) and Kirin et al., *Inorg. Chem.*, 44(15): 5405-5415 (2005)).

Another embodiment of the invention further provides an antibody, or antigen binding portion thereof, which specifically binds to a fragment or portion of GalNAcα1-3Gal described herein. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for GalNAcα1-3Gal. Desirably, the antibody is specific for GalNAcα1-3Gal such that there is minimal cross-reaction with other carbohydrate moieties.

Methods of testing antibodies for the ability to bind to any fragment or portion of GalNAcα1-3Gal are known in the art and include, for example, any antibody-antigen binding assay, such as, for example, radioimmunoassay (RIA), ELISA, Western blot, immunoprecipitation, and competitive inhibition assays (see, e.g., Janeway et al., infra, and U.S. Patent Application Publication No. 2002/0197266 A1).

Suitable methods of making antibodies are known in the art. For instance, standard hybridoma methods are described in, e.g., Köhler and Milstein, *Eur. J. Immunol.*, 5: 511-519 (1976), Harlow and Lane (eds.), *Antibodies: A Laboratory Manual*, CSH Press (1988), and C. A. Janeway et al. (eds.), *Immunobiology*, 5$^{th}$ Ed., Garland Publishing, New York, N.Y. (2001)). Alternatively, other methods, such as EBV-hybridoma methods (Haskard and Archer, *J. Immunol. Methods*, 74(2): 361-67 (1984), and Roder et al., *Methods Enzymol.*, 121: 140-67 (1986)), and bacteriophage vector expression systems (see, e.g., Huse et al., Science, 246: 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1).

In an embodiment, phage display furthermore can be used to generate the antibody of the invention. In this regard, phage libraries encoding antigen-binding variable (V) domains of antibodies can be generated using standard molecular biology and recombinant DNA techniques (see, e.g., Sambrook et al. (eds.), *Molecular Cloning, A Laboratory Manual*, 3$^{rd}$ Edition, Cold Spring Harbor Laboratory Press, New York (2001)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539, 5,585,089 and 5,693,761. Humanized antibodies can also be generated using the antibody resurfacing technology described in U.S. Pat. No. 5,639,641 and Pedersen et al., J. Mol. Biol., 235: 959-973 (1994).

A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., *Protein Engineering*, 7: 697-704 (1994)). Antibody fragments of the invention, however, are not limited to these exemplary types of antibody fragments.

In another embodiment, the antibody, or antigen binding fragment thereof, is modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold or magnetic particles).

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, protein A/G immunoprecipitation chromatography, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The antibodies of the present invention can be employed to prepare antigen-antibody affinity columns, which may be used for the purification of the antigen or to separate cells or other substrates that are bound to the antigen. For example, gel supports or beads can be activated with various chemical compounds, e.g., cyanogen bromide, N-hydroxysuccinimide esters, and antibodies can be bound thereto. More particularly, and by way of example, antibodies can be added to Affigel-10 (BioRad, Hercules, Calif.), a gel support which is activated with N-hydroxysuccinimide esters, such that the antibodies form covalent linkages with the agarose gel bead support. The antibodies are then coupled to the gel via amide bonds with a spacer arm. The remaining activated esters are then quenched with ethanolamine HCl, 1 M, pH 8. The column is washed with water, followed by 0.23 M glycine HCl, pH 2.6, to remove any non-conjugated antibody or extraneous protein. The column is then equilibrated in phosphate buffered saline (PBS), pH 7.3, with appropriate detergent, and the sample materials, i.e., cell culture supernatants or cell extracts, for example, containing the cancer-specific antigens (e.g., prepared using appropriate membrane solubilizing surfactants) are slowly passed over the column. The column is washed with PBS/surfactant until the optical density falls to background. The protein is then eluted from the column with 0.23 M glycine-HCl, pH 2.6/surfactant. The purified antigens are then dialyzed against PBS/surfactant.

Another aspect of the present invention relates to therapeutic methods for the treatment of cancer patients, particularly individuals afflicted with cancers involving cells displaying the GalNAcα1-3Gal antigen, which is expressed in cancers from many cells or tissues, including skin and squamous cells, cervix, esophagus, larynx, oral, nasopharyngeal, salivary glands, stomach, colon, rectum, liver, bile duct, pancreas, lung, bone, soft tissue, melanoma, breast, ovarian, prostate, penis, testis, urinary tract, bladder, kidney, brain, thyroid, adrenal, thymus, endocrine pancreas, eye, and combinations thereof.

Methods of detecting the presence of cancer in a subject and methods of treating or preventing cancer in a subject are further provided by the present invention. The inventive method of detecting the presence of cancer in a subject (e.g., a patient) comprises (i) contacting a sample comprising cells of the cancer with any of the inventive antibodies, or antigen binding fragments thereof, described herein, thereby forming a complex, and (ii) detecting the complex, wherein detection of the complex is indicative of the presence of cancer in the subject.

The present invention further provides a method for localizing cancer cells in a patient, especially cancer cells expressing the GalNAcα1-3Gal antigen, comprising: (a) administering to the patient a detectably-labeled monoclonal antibody of the invention, or binding fragment thereof; (b) allowing the detectably-labeled (e.g., radiolabeled; fluorochrome labeled, or enzyme labeled, for example, via ELISA) monoclonal antibody, or binding fragment thereof, to bind to the cancer cells within the patient; and (c) determining the location of the labeled monoclonal antibody or binding fragment thereof, within the patient.

The therapeutic methods encompassed by the present invention involve primary tumors or cancers, as well as metastases. As an example, in one embodiment, a method for inhibiting or killing cancer cells comprises administering to a patient one or more of the monoclonal antibodies, or a binding fragment thereof, having specificity for the cancer cells, as described above, under conditions sufficient for the binding of the monoclonal antibody, or binding fragment, to tumor or cancer cells in the patient. Antibody-mediated treatment or therapy of the present invention may be accompanied by treatments that are directed to tumor or cancer cells, for example, radiation, chemotherapy, and the like, as well as by adjunctive therapies to enhance the immune system's attack on the opsonized cancer or tumor cells, following the above-described treatment/therapy procedures.

In an embodiment, a growth factor, lymphokine, or cytokine is co-administered with one or more of the monoclonal antibodies, for example, erythropoietin and/or GM-CSF (granulocyte/macrophage colony-stimulating factor), to stimulate the patient's white blood cells and support the immunocompetence status of the patient. In another embodiment, chimeric or fusion antibodies, or other recombinant antibodies of the present invention may be used in therapies and treatment. For example, a fusion protein molecule comprising at least the antigen-binding region or fragment of an antibody of the invention, joined to at least a functionally active or bioactive portion of a second protein having anti-tumor or cancer effects, e.g., a lymphokine or oncostatin, may be used to treat the cancer, particularly, in vivo. In an alternate embodiment, a chimeric antibody is prepared, wherein the antigen binding portion or site is joined to a human Fc molecule of an immunoglobulin, e.g., IgG1, to promote antibody-dependent mediated cytotoxicity or complement-mediated cytotoxicity. Recombinant techniques and protocols as known and practiced in the art (e.g., U.S. Pat. No. 6,106,833 to Ring et al.) may be used to construct bispecific or bifunctional chimeric antibodies wherein one of the binding specificities is that of the antibody according to the present invention.

The term "biological response modifiers" is meant to encompass substances that are involved in modifying the immune response in such manner as to enhance the destruction of the antigen-bearing tumor for which the monoclonal antibodies of the invention is specific. Examples of immune response modifiers include such compounds as lymphokines. Lymphokines include tumor necrosis factor, interleukins, e.g., IL-1 through IL-15, lymphotoxin, macrophage activating factor (MAF), migration inhibition factor (MIF), colony stimulating factor (CSF), and interferon. Interferons with which the monoclonal antibodies of the invention can be labeled include alpha-interferon, beta-interferon and gamma-interferon and their subtypes.

The labeled or unlabeled monoclonal antibodies of the present invention can also be used in combination with therapeutic agents such as those described above. It is also contemplated that one or more of the embodiments of the present invention include therapeutic combinations comprising the monoclonal antibody of the invention and immunomodulators and other biological response modifiers. Thus, for example, the monoclonal antibodies of the invention can be used in combination with alpha-interferon. This treatment method enhances monoclonal antibody targeting of cancers by increasing the expression of monoclonal antibody reactive antigen by the cancer cells (Greiner et al., *Science,* 235: 895 (1987)). In an alternative embodiment, the monoclonal antibodies of this invention may be used, for example, in combination with gamma-interferon to activate and increase the expression of Fc receptors by effector cells, which, in turn, results in an enhanced binding of the monoclonal antibody to the effector cell and killing of target tumor cells. Those of skill in the art will be able to select from the various biological response modifiers to create a desired effector function which enhances the efficacy of the monoclonal antibodies of the invention.

Drugs that can be conjugated to the monoclonal antibodies of the present invention include non-proteinaceous as well as proteinaceous compounds. The term "non-proteinaceous drugs" encompasses compounds classically referred to as drugs, for example, mitomycin C, daunorubicin, and vinblastine. The proteinaceous drugs with which the monoclonal antibodies of the invention can be labeled include immunomodulators and other biological response modifiers.

Lectins are proteins, usually isolated from plant material, which bind to specific sugar moieties. Many lectins are also able to agglutinate cells and stimulate lymphocytes. Ricin is a toxic lectin that has been used immunotherapeutically. In an embodiment, this is accomplished by binding the alpha-peptide chain of ricin, which is responsible for toxicity, to the antibody molecule of the present invention to enable site specific delivery of the toxic effect.

Toxins are poisonous substances produced by plants, animals, or microorganisms that, in sufficient dose, are often lethal, especially to cells in the vicinity. Diphtheria toxin (DT), a substance produced by *Corynebacterium diphtheria*, can be used therapeutically. DT consists of an alpha and beta subunit which under proper conditions can be separated. The toxic alpha component can be bound to an antibody and used for site specific delivery to a cell bearing an antigen for which the monoclonal antibodies of the invention are specific. Other therapeutic agents which can be coupled to the monoclonal antibodies of the invention are known, or can be easily ascertained, by those of ordinary skill in the art.

In another embodiment, the present invention comprises therapeutic methods utilizing the described monoclonal antibodies, or binding fragments thereof, to which a cytotoxic agent has been bound, affixed or coupled. The binding of the cytotoxic antibodies or binding fragments thereof, to the tumor or cancer cells inhibits the growth of the cells directly and optimally kills the cells. Examples of suitable cytotoxic agents include chemotherapeutic compounds, drugs (e.g., Garnett and Baldwin, Cancer Res., 46, 2407-24112 (1986)), prodrugs, enzymes, photoactivated toxins, or radioactive agents. Cytotoxic agents include, but are not limited to, ricin A chain, abrin A chain, modeccin A chain, gelonin, melphalan, bleomycin, adriamycin, daunomycin, or pokeweed antiviral proteins (PAP, PAPII, or PAP-S).

One of ordinary skill in the art will realize that there are numerous radionuclides and chemocytotoxic agents that can be coupled to cancer-specific antibodies by well-known techniques and delivered to a site to specifically destroy tumor cells and tissue. (See, e.g., U.S. Pat. No. 4,892,827; and Pastan et al., Cell, 47: 641-648 (1986)). Examples of photoactivated toxins include dihydropyridine- and omega-conotoxin (Schmidt et al., *J. Biol. Chem.*, 266(27): 18025-18033 (1991)). Nonlimiting examples of imaging and cytotoxic reagents that are suitable for use include $^{125}$I, $^{123}$I, $^{111}$In (e.g., Sumerdon et al., *Nucl. Med. Biol.*, 17: 247-254 (1990)), $^{99m}$Tc, $^{32}$P, $^{3}$H and $^{14}$C; fluorescent labels such as fluorescein and rhodamine; chemiluminescent labels such as luciferin, and paramagnetic ions for use in magnetic resonance imaging (e.g., Lauffer et al., *Magnetic Resonance in Medicine*, 22: 339-342 (1991)).

In an embodiment, antibodies of the present invention are labeled with such reagents using protocols and techniques known and practiced in the art. See, for example, *Radioimmunotherapy of Cancer*, (Paul G. Abrams et al., eds.) Marcel Dekker, Inc., New York, (2000); Colcer et al., *Meth. Enzymol.*, 121: 802-816 (1986); and David M. Goldenberg, *Cancer Therapy with Radiolabeled Antibodies*, CRC Press, Inc., (1995), for techniques relating to the radiolabeling of antibodies. Yttrium-90 labeled monoclonal antibodies have been described for maximizing the dose delivered to the tumor or cancer cells and/or tissue, while limiting toxicity to normal tissues (e.g., Goodwin and Meares, *Cancer Supplement*, 80: 2675-2680 (1997)). Other cytotoxic radionuclides including, but not limited to, Copper-67 ($^{67}$Cu), Iodine-131 ($^{131}$I) and Rhenium-186 can also be used for labeling monoclonal antibodies.

The detectable/detecting label used is selected according to the imaging modality to be used. For example, radioactive labels, such as Indium-111 ($^{111}$In), Technetium-99 ($^{99}$Tc), or Iodine 131, ($^{131}$I) can be used for planar scans or for single photon emission computed tomography (SPECT). Also, positron-emitting labels such as Fluorine-19 ($^{19}$F) can be used in positron emission tomography (PET). Paramagnetic ions, such as Gadolinium(III) or Manganese(II) can be used in magnetic resonance imaging (MRI). The monoclonal antibodies can also be labeled with radio-opaque labels for the visualization of cancer cells after injection, for example, by X-ray, CAT scan, or MRI.

In using radioisotopically conjugated monoclonal antibodies of the invention for immunotherapy, certain isotopes may be more preferable than others depending on such factors as leukocyte distribution as well as isotope stability and emission. If desired, the tumor cell distribution can be evaluated by the in vivo diagnostic techniques described above. Depending on the malignancy, some emitters may be preferable to others. In general, alpha and beta particle-emitting radioisotopes are preferred in immunotherapy. For example, if an animal has solid tumor foci, as in a carcinoma, a high energy beta emitter capable of penetrating several millimeters of tissue, such as $^{90}$Y, may be preferable. On the other hand, if the malignancy consists of simple target cells, as in the case of leukemia, a shorter range, high energy alpha emitter, such as $^{212}$Bi, may be preferable. Examples of radioisotopes which can be bound to the monoclonal antibodies of the invention for therapeutic purposes are $^{125}$I, $^{131}$I, $^{90}$Y, $^{67}$Cu, $^{212}$Bi, $^{211}$At, $^{212}$Pb, $^{47}$Sc, $^{109}$Pd, and $^{188}$Re.

Other covalent and non-covalent modifications of the monoclonal antibodies of the present invention, or their binding fragments, as described herein, are further encompassed for use in the present invention. Such modifications are meant to include agents which are co-administered with, or are administered subsequent to, the administration of the antibody (ies), or fragments thereof, for inhibition or killing of the cells to which the antibody (ies) or fragments bind. For example, immunotoxins conjugated to monoclonal antibodies have been found to be efficacious in animal models. The conjugation of monoclonal antibodies with ribosome-inactivating proteins (e.g., ricin A-chain, ricinus agglutinin, or viscumin) or photoinactivating agents has been described (see, e.g., D. B. Papkovskii et al., *Biomed. Sci.*, 1(4): 401-406 (1990)). In addition, pokeweed antiviral protein (PAP) has the ability to disrupt anti-apoptotic complexes or inhibit protein synthesis within the target cell, ultimately resulting in the death of the cell. Further, a number of small molecules that inhibit tyrosine kinases can be specifically targeted to cancer cells as growth factor conjugates, and which can be administered with the monoclonal antibodies, or fragments thereof, according to the present invention.

In a related embodiment of the present invention, the monoclonal antibodies according to the present invention can be used for immunotherapy, either coupled or uncoupled with a therapeutic agent. These therapeutic agents can be coupled either directly or indirectly to the described monoclonal antibodies, using techniques routinely practiced in the art. One example of indirect coupling is by the use of a spacer moiety. Spacer moieties, in turn, can be either insoluble or soluble (e.g., Dieher et al., *Science,* 231: 148 (1986)) and can be selected to enable drug release from the monoclonal antibody molecule at the target site. Non-limiting examples of therapeutic agents which can be coupled to the monoclonal antibodies of the invention for anti-cancer immunotherapy are drugs, radioisotopes, lectins, and toxins.

In an embodiment, the antibodies, or binding fragments thereof, are delivered parenterally, such as by intravenous, subcutaneous, or intraperitoneal administration, e.g., injection. Suitable buffers, carriers, and other components known in the art can be used in formulating a composition comprising the antibody or fragments for suitable shelf-life and compatibility for the administration. These substances may include ancillary agents such as buffering agents and protein stabilizing agents (e.g., polysaccharides).

More specifically, therapeutic formulations of the antibodies, or binding fragments thereof, are prepared for storage by mixing the antibodies or their binding fragments, having the desired degree of purity, with optional physiologically acceptable carriers, excipients, or stabilizers (*Remington's Pharmaceutical Sciences,* 17th edition, (Ed.) A. Osol, Mack Publishing Company, Easton, Pa., (1985)), in lyophilized form or in the of aqueous solutions. Acceptable carriers, excipients or stabilizers are nontoxic to recipients at the dosages and concentrations employed, and include, for example, buffers such as phosphate, citrate, and other organic acids; antioxidants including ascorbic acid; low molecular weight (e.g., about 10-15 amino acid residues or less) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ (polysorbates), PLURONICS™ (block copolymers of ethylene oxide (EO) and propylene oxide (PO)) or polyethylene glycol (PEG).

The antibodies, or binding fragments thereof, also may be entrapped in microcapsules prepared, for example, by coacervation techniques or by interfacial polymerization (for example, hydroxymethylcellulose or gelatin-microcapsules and poly-[methylmethacylate] microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences,* supra.

Antibodies or their binding fragments to be used for in vivo administration must be sterile. This is readily accomplished by filtration through sterile filtration membranes, prior to, or following lyophilization and reconstitution. The antibodies, or binding fragments thereof, ordinarily will be stored in lyophilized form or in solution.

Therapeutic antibody compositions generally are placed into a container having a sterile access port, for example, an intravenous solution bag or vial having a stopper pierceable by a hypodermic injection needle. The route of administration of the antibodies, or binding fragments thereof, in accordance with the present invention, is in accord with known methods, e.g., injection or infusion by intravenous, intraperitoneal, intramuscular, intrarterial, subcutaneous, intralesional routes, by aerosol or intranasal routes, or by sustained release systems as noted below. The antibodies, or binding fragments thereof, are administered continuously by infusion or by bolus injection.

An effective amount of antibody to be employed therapeutically will depend, for example, upon the therapeutic and treatment objectives, the route of administration, the age, condition, and body mass of the patient undergoing treatment or therapy, and auxiliary or adjuvant therapies being provided to the patient. Accordingly, it will be necessary and routine for the practitioner to titer the dosage and modify the route of administration, as required, to obtain the optimal therapeutic effect. A typical daily dosage might range from about 0.01 mg/kg to up to about 100 mg/kg or more, preferably from about 0.1 to about 10 mg/kg/day depending on the above-mentioned factors. Typically, the clinician will administer antibody until a dosage is reached that achieves the desired effect. The progress of this therapy is easily monitored by conventional assays.

Various adjuvants may be used to increase the immunological response to the antigen and to elicit specific antibodies according to the present invention. Depending on the host species to be immunized, adjuvants may include, but are not limited to, Freund's (complete and incomplete), mineral gels, such as aluminum hydroxide, surface active agents, such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum.*

The antibodies of the present invention are also useful for in vitro diagnostic applications for the detection of cancer cells that possess the GalNAcα1-3Gal antigen for which the antibodies are specific. As detailed above, in vitro diagnostic methods include immunohistological or immunohistochemical detection of tumor cells (e.g., on human tissue, or on cells dissociated from excised tumor specimens), or serological detection of tumor associated antigens (e.g., in blood samples or other biological fluids). Immunohistochemical techniques involve staining a biological specimen, such as a tissue specimen, with one or more of the antibodies of the invention and then detecting the presence on the specimen of antibody-antigen complexes comprising antibodies bound to the cognate antigen. The formation of such antibody-antigen complexes with the specimen indicates the presence of cancer in the tissue.

Detection of the antibody on the specimen can be accomplished using techniques known in the art such as immunoenzymatic techniques, e.g., immunoperoxidase staining technique, or the avidin-biotin technique, or immunofluorescence techniques (see, e.g., Ciocca et al., *Meth. Enzymol.,* 121: 562-79 (1986), and *An Introduction to Immunology,* (C. V. Rao), 119-140, Alpha Science International, UK (2002)). Serologic diagnostic techniques involve the detection and quantification of tumor-associated antigens that have been secreted or "shed" into the serum or other biological fluids of patients thought to be suffering from cancer, as mentioned above. Such antigens can be detected in the body fluids using techniques known in the art, such as radioimmunoassays (RIA) or enzyme-linked immunoabsorbant assays (ELISA), wherein antibody reactive with the shed antigen is used to detect the presence of the antigen in a fluid sample (See, e.g., Uotila et al., *J. Immunol. Methods,* 42: 11 (1981) and Fayed et al., *Disease Markers,* 14: 155-160 (1998)).

The antibody or antibodies which is/are used in the context of the present invention can, themselves, be linked to a detectable label, such as, for example, in an ELISA assay. Such a detectable label allows for the presence of, or the amount of the primary immune complexes to be determined. Alternatively, the first added component that becomes bound within the primary immune complexes can be detected by means of a second binding ligand that has binding affinity for the first antibody. In these cases, the second binding ligand is itself, often an antibody, which can be termed a "secondary" antibody. The primary immune complexes are contacted with the labeled, secondary binding ligand, or antibody, for a period of time sufficient to allow the formation of secondary immune complexes. The secondary immune complexes are then washed to remove any non-specifically bound labeled secondary antibodies or ligands, and the remaining label in the secondary immune complexes is then detected.

In an embodiment, a method of detecting the presence and/or extent of cancer in a patient is provided, comprising: determining the level of the GalNAc$\alpha$1-3Gal antigen in a sample of bodily fluid or a tissue section from the patient and correlating the quantity of the antigen with the presence and extent of the cancer disease in the patient. In one embodiment, the GalNAc$\alpha$1-3Gal antigen is detected by (1) adding monoclonal antibody 132-3 to the sample or tissue section; (2) adding goat anti-mouse IgG antibody conjugated with peroxidase; (3) fixing with diaminobenzidene and peroxide, and (4) examining the sample or section, wherein reddish brown color indicates that the cells bear the antigen. According to the methods of the present invention, the effectiveness of a cancer treatment may be monitored by periodically measuring changes in the level of the GalNAc$\alpha$1-3Gal antigen in a body fluid sample taken from a patient undergoing the therapy, and correlating the change in level of the antigen with the effectiveness of the therapy, wherein a lower level of antigen determined at a later time point relative to the level of antigen determined at an earlier time point during the course of therapy indicates effectiveness of the therapy for the cancer disease.

Further methods of the present invention include the detection of primary immune complexes by a two-step approach. A second binding ligand, such as an antibody, that has binding affinity for the first antibody is used to form secondary immune complexes, as described above. After washing, the secondary immune complexes are contacted with a third binding ligand or antibody that has binding affinity for the second antibody, for a period of time sufficient to allow the formation of immune complexes (tertiary immune complexes). The third ligand or antibody is linked to a detectable label, allowing detection of the tertiary immune complexes thus formed.

When the monoclonal antibodies of the present invention are used in combination with various therapeutic agents, the administration of the monoclonal antibody and the therapeutic agent usually occurs substantially contemporaneously. The term "substantially contemporaneously" means that the monoclonal antibody and the therapeutic agent are administered reasonably close together with respect to time. Usually, it is preferred to administer the therapeutic agent before the monoclonal antibody. For example, the therapeutic agent can be administered about 1 to 6 days before the monoclonal antibody. The administration of the therapeutic agent can be daily, or at any other interval, depending upon such factors, for example, as the nature of the tumor, the condition of the patient and the half-life of the agent.

Using the monoclonal antibodies of the present invention, it is possible to design therapies combining all of the characteristics described herein. In a given situation, it may be desirable to administer a therapeutic agent, or agents, prior to the administration of the monoclonal antibodies of the invention, in combination with effector cells and the same, or different, therapeutic agent or agents. For example, it may be desirable to treat patients with malignant disease by first administering gamma-interferon and interleukin-2 daily for 3 to 5 days, and on day 5 administer the monoclonal antibody of the invention in combination with effector cells, as well as gamma-interferon, and interleukin-2.

The dosage ranges for the administration of the monoclonal antibodies of the invention are those large enough to produce the desired effect in which the symptoms of the malignant disease are ameliorated. The dosage should not be so large as to cause adverse side effects, such as unwanted cross-reactions, anaphylactic reactions, and the like. Generally, the dosage will vary with the age, condition, sex and extent of disease of the patient and can be determined by one of skill in the art. The dosage can be adjusted by the individual physician in the event of any complication. Dosage can vary from about 0.01 mg/kg to about 2000 mg/kg, preferably about 0.1 mg/kg to about 500 mg/kg, or preferably about 0.1 mg/kg to about 10 mg/kg, in one or more dose administrations daily, for one or several days.

Generally, when the monoclonal antibodies of the present invention are administered conjugated with therapeutic agents, lower dosages, comparable to those used for in vivo immunodiagnostic imaging, can be used. The monoclonal antibodies of the invention can be administered parenterally by injection or by gradual perfusion over time. The monoclonal antibodies of the invention can be administered intravenously, intraperitoneally, intramuscularly, subcutaneously, intracavity, or transdermally, alone or in combination with effector cells. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

As mentioned hove, anti-idiotypic monoclonal antibodies to the antibodies according to the present invention may be used in therapies and treatments in active tumor immunization and tumor therapy (See, for example, *Radioimmunotherapy of Cancer*, supra).

In an embodiment, the monoclonal antibodies, or binding fragments thereof, according to the present invention, are used to quantitatively or qualitatively detect the presence of the cancer-specific antigen, GalNAc$\alpha$1-3Gal, on cancer cells. This can be achieved, for example, by immunofluorescence techniques employing a fluorescently labeled antibody, coupled with light microscopic, flow cytometric, or fluorometric detection. In addition, the antibodies, or binding fragments thereof, according to the present invention may additionally be employed histologically, as in immunofluorescence, immunoelectron microscopy, or non-immuno assays, for in situ detection of the cancer-specific antigen on cells, such as for use in monitoring, diagnosing, or detection assays.

In yet another embodiment, in situ detection is accomplished by removing a histological specimen from a patient, and applying thereto a labeled antibody according to this invention. The antibody, or antigen-binding fragment thereof, is preferably applied by overlaying the labeled antibody or fragment onto the biological sample. Through the use of such a procedure, it is possible to determine not only the presence of the antigen, or conserved variants, or peptide fragments, but also its distribution in the examined tissue. Those of ordinary skill in the art will readily recognize that any of a wide variety of histological methods, e.g., staining procedures, can be modified in order to achieve such in situ detection.

In another embodiment, an immunoassay and other assays are contemplated for the antigen GalNAcα1-3Gal. Such assays comprise incubating a sample, such as a biological fluid, tissue extract, freshly harvested cells, or lysates of cells that have been incubated in cell culture, in the presence of a detectably-labeled antibody that recognizes the antigen, GalNAcα1-3Gal, such as the cancer-specific monoclonal antibodies of the present invention, or binding fragments thereof. Thereafter, the bound antibody, or binding fragment thereof, is detected by a number of techniques well known in the art.

In an immunoassay of the present invention, a biological sample may be brought into contact with, and immobilized onto, a solid phase support or carrier, such as nitrocellulose, or other solid support or matrix, which is capable of immobilizing cells, cell particles, membranes, or soluble proteins. The support is then washed with suitable buffers, followed by treatment with the detectably-labeled antibody. The solid phase support is then washed with buffer a second time to remove unbound antibody. The amount of bound label on the solid support is then detected by conventional means. Accordingly, in another embodiment of the present invention, compositions are provided comprising the monoclonal antibodies, or binding fragments thereof, bound to a solid phase support, such as described herein.

By solid phase support, or carrier, or matrix, is meant any support capable of binding an antigen or an antibody. Well-known supports or carriers include glass, plastic, nylon wool, polystyrene, polyethylene, polypropylene, dextran, nylon, amylases, films, resins, natural and modified celluloses, polyacrylamides, agarose, alumina gels, gabbros, and magnetite. The nature of the carrier can be either soluble to some extent, or insoluble for the purposes of the present invention. The support material may have virtually any possible structural configuration as long as the coupled molecule is capable of binding to an antigen or antibody. Thus, the support configuration may be spherical, as in a bead, cylindrical, as in the inside surface of a test tube, or the external surface of a rod. Alternatively, the surface may be flat, such as a sheet, film, test strip, stick, and the like.

In an embodiment, the solid support is inert to the reaction conditions for binding and may have reactive groups, or activated groups, in order to attach the monoclonal antibody, a binding fragment, or the binding partner of the antibody. The solid phase support can also be useful as a chromatographic support, such as the carbohydrate polymers SEPHAROSE™ (crosslinked agarose beads), SEPHADEX™ (crosslinked dextran gel), or agarose. Indeed, a large number of such supports for binding antibody or antigen are commercially available and known to those having skill in the art.

The binding activity for a given antibody may be determined by well-known methods. With respect to the cancer specific antibodies of the present invention, numerous ways to detectably label such protein molecules are known and practiced in the art. For example, in an embodiment, the antibodies of the present invention can be detectably labeled is by linking the antibody to an enzyme, e.g., for use in an enzyme immunoassay (EIA), (See, e.g., E. Ishikawa, *Ultrasensitive and Rapid Enzyme Immunoassay*, (S. Pillai et al., eds.) Elsevier (1999)). The enzyme that is bound to the antibody reacts with an appropriate substrate, preferably a chromogenic substrate, so as to produce a chemical moiety which can be detected, for example, by spectrophotometric, fluorometric, or by visual detection means. Nonlimiting examples of enzymes which can be used to detectably label the antibodies include malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, ribonuclease, urease, catalase, glucose-6-phosphate dehydrogenase, glucoamylase and acetylcholinesterase. The detection can be accomplished by chrometric methods, which employ a chromogenic substrate for the enzyme, or by visual comparison of the extent of enzymatic reaction of a substrate compared with similarly prepared standards or controls.

A variety of other immunoassays may also be used for detection. For example, in an embodiment, the antibodies of the present invention, or binding fragments thereof, are labeled with a radioisotope, a radioimmunoassay (RIA) can be used to detect cancer-specific antigens (e.g., *Radioimmunotherapy of Cancer*, supra, and *Cancer Therapy with Radiolabeled Antibodies*, supra). The radioactive isotope label can be detected by using a gamma counter or a scintillation counter or by radiography.

The antibodies of the present invention or their antigen-binding fragments can also be labeled using a fluorescent compound. When the fluorescently labeled antibody is exposed to light of the proper wavelength, its presence can then be detected due to fluorescence. Some of the most commonly used fluorescent labeling compounds include fluorescein isothiocyanate, rhodamine, phycoerythrin, phycocyanin, allophycocyanin, o-phthaldehyde and fluorescamine. Detectably labeled fluorescence-emitting metals, such as $^{152}$Eu, or others of the lanthanide series, can be used to label the antibodies, or their binding fragments, for subsequent detection. The metals can be coupled to the antibodies via such metal chelating groups as diethylenetriaminepentacetic acid (DTPA), or ethylenediaminetetraacetic acid (EDTA).

In an alternate embodiment, the antibodies of the present invention can also be detectably labeled by coupling them to a chemiluminescent compound. The presence of the chemiluminescent-tagged antibody is then determined by detecting the presence of luminescence that develops during the course of a chemical reaction. Examples of particularly useful chemiluminescent labeling compounds include, without limitation, luminol, isoluminol, theromatic acridinium ester, imidazole, acridinium salt and oxalate ester. Similarly, a bioluminescent compound may be used to label the antibodies of the present invention. Bioluminescence is a type of chemiluminescence found in biological systems in which a catalytic protein increases the efficiency of the chemiluminescent reaction. The presence of a bioluminescent protein is determined by detecting the presence of luminescence. Useful bioluminescent labeling compounds include, for example, luciferin, luciferase and aequorin.

A diagnostic method according to the invention comprises, in an embodiment, administering, introducing, or infusing the monoclonal antibodies or their binding fragments as described herein, with or without conjugation to a detectable moiety, such as a radioisotope. After administration or infusion, the antibody or binding fragment binds to the tumor or cancer cells, after which the location of the bound antibodies or fragments is detected. For detectably labeled antibodies or fragments, for example, those labeled with a radioisotope, imaging instrumentation may be used to identify the location of the agent within the body. For unlabeled antibodies or fragments, a second detectable reagent may be administered, which locates the bound antibodies or fragments so that they can be suitable detected. Similar methods have been employed for other antibodies, and the skilled practitioner will be aware of the various methods suitable for imaging the location of detectably bound antibodies or fragments within the body. As a general guidance, about 10-1000 μg, preferably about 50-500 μg, more preferably about 100-300 μg, most preferably about 200-300 μg of a Protein G, or Protein A purified monoclonal antibody is administered. For mice, for example, using 200 μg monoclonal antibody and intraperitoneal (i.p.) administration, monoclonal antibody is injected three times a week for three weeks. For 300 μg monoclonal antibody and intraperitoneal (i.p.) administration, monoclonal antibody is injected two times a week for three weeks. Applicable doses for humans include about 100-200 μg/kg, or about 350-700 mg/m².

It is understood by those of ordinary skill in the art, that a cocktail of different monoclonal antibodies, such as a mixture of the specific monoclonal antibodies described herein, or their binding fragments, in an embodiment, may be administered; if necessary or desired, for cancer treatment. Indeed, using a mixture of monoclonal antibodies, or binding fragments thereof, in a cocktail to target several antigens, or different epitopes, on cancer cells, is an advantageous approach, particularly to prevent evasion of tumor cells and/or cancer cells due to downregulation of one of the antigens.

In another embodiment, the present invention assists in the diagnosis of cancers and tumors by the identification and measurement of the cancer-specific antibody GalNAcα1-3Gal, in body fluids, such as blood, serum, plasma, sputum and the like. For those cancers that express the antigen described herein, the ability to detect the antigen provides early diagnosis, thereby affording the opportunity for early treatment. Early detection is especially important for cancers difficult to diagnose in their early stages.

Moreover, the level of GalNAcα1-3Gal antigen detected and measured in a body fluid sample, such as blood, provides a means for monitoring the course of therapy for the cancer or tumor, including, but not limited to, surgery, chemotherapy, radiation therapy, the therapeutic methods of the present invention, and combinations thereof. By correlating the level of the antigen in the body fluid with the severity of disease, the level of such antigen can be used to indicate successful removal of the primary tumor, cancer, and/or metastases, for example, as well as to indicate and/or monitor the effectiveness of other therapies over time. For example, a decrease in the level of the cancer or tumor-specific antigen over time indicates a reduced tumor burden in the patient. By contrast, no change, or an increase, in the level of antigen over time indicates ineffectiveness of therapy, or the continued growth of the tumor or cancer.

In another embodiment, the present invention relates to a method of diagnosing the presence of cancer in a patient, comprising: (a) measuring the levels of the GalNAcα1-3Gal antigen in a sample of cells, tissues, or body fluids of the patient; and (b) comparing the measured levels of the GalNAcα1-3Gal antigen of (a) with levels of the GalNAcα1-3Gal antigen in cells, tissues, or body fluids from a normal human control, wherein an increase in the measured levels of the GalNAcα1-3Gal antigen in the patient versus the normal control is associated with the presence of the cancer. Also provided is a method of imaging cancer in a patient, comprising administering to the patient the antibody, wherein the antibody is detectably labeled with paramagnetic ions or with a radioisotope.

In an embodiment, the invention also provides methods for prognosticating the serverity or outcome of the disease based on the level of monoclonal antibody binding to GalNAcα1-3Gal antigen. The method comprises assaying a sample of the cancer cells or tumors or tissues or body fluids from a patient and comparing the level or amount of GalNAcα1-3Gal antigen present in the sample from the patient with the levels with those obtained from normal human controls or cancer specific controls. In the prognostication assay, those patients who have cancer cells or tumors or tissues or body fluids which express GalNAcα1-3Gal antigen are deemed to have a higher likelihood of survival 5-years post-treatment, when compared to cancer specific controls which do not express the antigen.

EXAMPLES

Unless otherwise indicated, all chemicals and organic solvents identified in the present application are from commercially available sources and used without further purification. Vectastain ABC kit (Vector labs, Burlingame, Calif.), including biotinylated goat anti-mouse mouse IgM secondary antibody solution, was used for blocking and secondary reagent for 81FR2.2. *Dolichos biflorus* agglutinin (DBA) lectin (Vector labs, Burlingame, Calif.) was used with Vectastain ABC universal kit. Vectastain ABC kit for rabbit IgG antibody was used for 132-3 and PolyTn. Goat anti-rabbit IgG-alkaline phosphatase conjugate (Southern Biotech, Birmingham, Ala.) was used in the ELISA assay. Fluorophore Cy3 labeled goat anti-rabbit IgG, Cy3 labeled anti-mouse IgM (Jackson ImmunoResearch Laboratories, Inc., West Grove, Pa.) and Cy3 labeled streptavidin (Vector labs, Burlingame, Calif.) were used in the carbohydrate microarray.

All tissue samples taught herein were formalin fixed and paraffin coated. The multiple organ human tissue microarray slides are from U.S. Biomax Inc. (Rockville, Md.). The cervical cancer tissue microarray slides are from Imgenex Inc. (San Diego, Calif.). Cervical cancer tissues from fifteen different individuals were obtained from Capital Bioscience Inc. (Gaithersburg, Md.). All tissues were classified using TMN system, histotype and stage grading according to the World Health Organization criteria. Patient survival information was available for 48 cervical cancer samples.

Example 1

In this example, the methods of immunization of the rabbits with the antigen are described.

Rabbits were immunized at Biocon, Inc. (Rockville, Md.). Briefly, GalNAcα1-3Gal {methyl N-{2-[(2-acetamido-2-deoxy-α-D-galactopyranosyl)-(1→3)-1-β-D-galactopyranosylsulfanyl]ethyl}glutamate} was coupled to keyhole limpet hemocyanin (KLH) via N-(3-dimethylaminopropyl)-N'-ethylcarbodiimide (EDC)/N-hydroxysuccinimide (NHS) activation of the terminal carboxylic acid followed by conjugation to KLH. The conjugates were dialyzed, diluted in phosphate buffer saline (PBS) to 1 mg/ml and sterile filtered. A rabbit was then inoculated with a 1:1 emulsion of 500 μg of antigen and complete Freund's adjuvant for antigen GalNAcα1-3Gal. The rabbit was boosted on day 21 with a 1:1 emulsion of 250 μg of antigen and Freund's incomplete adjuvant and then again on days 42, 63, 133 and 162, with a 1:1 emulsion of 125 μg of antigen and Freund's incomplete adjuvant. After the fifth boost, polyclonal antibody for the antigen was obtained from the rabbit serum. IgG ELISA titers to each antigen were over 30,000. The spleen was then harvested from the rabbits and used for hybridoma generation as reported previously (Spieker-Polet, H., et al., *Proc. Natl. Acad. Sci.* 92(20): 9348-9352 (1995)). Polyclonal antibodies to the antigen (Polyα1-3 for GalNAcα1-3Gal) were affinity purified (see Example 3, infra) prior to their use.

Example 2

In the following example, the methods for production of the hybridomas used to make the monoclonal antibodies are described.

Rabbits were immunized and their spleens harvested as described in Example 1. Approximately 4000 hybridomas were screened for antigen binding by ELISA and about 100 supernatants were positive for each antigen. The antigen positive hybridoma supernatants were tested for cross-reactivity with opposite antigen and with blood group A. Briefly, microtiter plates (Nunc, Roskilde, Denmark) were coated with 1 µg GalNAcα1-3Gal-BSA, or blood group A-BSA (Dextra Labs, UK) for 2 hours followed by blocking with 5% BSA/PBS buffer solution. The hybridoma solutions were diluted to 1:100 in 1% BSA/PBS, incubated for 2 hours at room temperature, and then incubated 1 hour with goat anti-rabbit IgG alkaline phosphatase conjugate at 1:1000 dilution. Next, 10 mM 4-methylumbelliferyl phosphate (MUP) in Tris buffer solution (10 mM Tris-HCl, 90 mM NaCl, pH 9.0) was added, and the fluorescent signal was detected by FLx800 microplate fluorescence reader (Bio-Tek instruments Inc., Winooski, Vt.). After this step, three positive hybridomas, specific for GalNAcα1-3Gal were obtained. The three hybridomas were subcloned at Epitomics Inc. (Burlingame, Calif.) using published methods well known in the art. Two selected hybridomas for GalNAcα1-3Gal and were successfully subcloned to 12 hybridomas. After subcloning, monoclonal antibodies were again tested on the carbohydrate array to confirm high selectivity (see FIGS. 2A-2D), and then the highest expressing clones were used for subsequent studies. Each antibody was aliquoted and stored at −20° C. until use. The best monoclonal antibodies against GalNAcα1-3Gal were derived from hybridomas 132-3 and 74-3. In addition to the monoclonal antibodies, polyclonal antibody to GalNAcα1-3Gal antigen (anti-GalNAcα1-3Gal="Polyα1-3") was affinity purified and its specificity was also profiled on the carbohydrate microarray.

TABLE 1

Final selected antibodies for GalNAcα1-3Gal

| Clone ID | Antigen | IgG OD[1] | IgG (ng/mL)[2] | Microarray Data Titers[3] |
|---|---|---|---|---|
| 74-3 | GalNAcα1-3Gal | 1.17 | 800 | GalNAcα1-3Gal = 1:500<br>GalNAcα = 1:10<br>GA2di = 1:5<br>GalNAcα1-4Gal = 1:5 |
| 132-3 | GalNAcα1-3Gal | 1.08 | 4400 | GalNAcα1-3Gal = 1:3200<br>GalNAcα = 1:100<br>GA2di = 1:10<br>GalNAcα1-4Gal = 1:10 |

[1]OD = optical density, from ELISA;
[2]concentration of IgG in cell culture supernatant;
[3]The lowest dilution of antibody that produced a signal 5 times over the background)

Example 3

The methods for purification of the monoclonal antibodies to GalNAcα1-3Gal are described in the example below.

GalNAcα1-3Gal-acid was prepared according to Springer, G. F., et al., *Cancer Detect. Prev.* 19(4): 374-380 (1995). GalNAcα1-3Gal-acid (150 mM in water, 30 µL) was combined with N-hydroxysuccinimide (NHS) in DMF (300 mM, 15 µL) and EDC (300 mM solution in 1:1 water/DMF, 15 µl). The reactions were kept at room temperature for 1 hour to pre-form the NHS esters. Aminoethyl agarose resin (2 ml each; Sigma-Aldrich, St. Louis, Mo., 4 atom spacer) was washed with water and centrifuged (1000 rpm, 5 minutes) in an ultrafree-MC PVDF filtration tube (0.22 µm, Millipore, Billerica, Mass.). Water was added to the dry resin (800 µL), 10×BICINE buffer (10 mM, pH 8.5, 200 µl) and GalNAcα1-3Gal-NHS solution. The mixture was shaken at room temperature for 2 hours and then treated with acetic anhydride (300 mM in DMF, 200 µl) for another 2 hours. The mixture was then centrifuged and washed with DMF/water, water and PBS buffer.

Affinity purification. Crude polyclonal anti-GalNAcα1-3Gal antibody (1 ml) was added to the corresponding dry resin (1 ml) in an ultrafree-MC PVDF tube, shaken at room temperature for 2 hours, and then centrifuged. The filtrate was removed and the resin was washed with PBS. The dry resin was treated with 1.2 ml of elution buffer [solution of GalNAc (400 mM), glycine (50 mM, pH 2.0), and NaCl (500 mM)] for 5 minutes. The mixture was centrifuged and immediately neutralized with PBS buffer (20×, 400 µl). The filtrate was dialyzed with PBS buffer (1 ml) in spin column (Millipore centrifugal filter devices, 2 ml max volume, polyethersulfone membrane, 50000 NMWL) for 6 times. The purified antibody was collected with PBS buffer (1 ml). The crude polyclonal antibody was then further purified with resins bound with other antigens (see below).

Removal of cross-reactive antibodies for Polyα1-3. Antibody (1 ml) was treated with a mixture of GalNAcα1-6Gal (100 µL), KLH (100 µL) and blood group A (100 µL) bound resin for 1.5 hours and centrifuged (1000 rpm, 5 minutes). The filtrate was collected and saved in refrigerator for future use.

Example 4

The formatting and printing of the carbohydrate array used to screen the monoclonal antibodies is described below.

Printing and the format of the carbohydrate array has been previously published (Manimala, J. C., et al., *Glycobiology* 17(8): 17C-23C (2007); Manimala, J. C., et al., *Angew. Chem. Int. Ed. Engl.* 45: 3607-3610 (2006); Manimala, J., et al., *ChemBioChem* 6(12): 2229-2241 (2005); Hsu, K. L., et al.; *Mol. BioSyst.* 4(6): 654-662 (2008); and Gildersleeve, J. C., et al., *Bioconjugate Chem.* 19(7): 1485-1490 (2008)). About 163 different glycoprotein or glycoconjugate samples were printed on the slides (TeleChem International, Inc., Sunnyvale, Calif.) in a duplicate manner with a total of 16 complete arrays on each slide. Antibodies were evaluated using previously published procedures with minor modifications. Briefly, the array was blocked by 200 µl 3% bovine serum albumin (BSA)/PBS for 2 hours, incubated with antibodies for 2 hours at room temperature, washed with PBS, and then incubated with 50 µl of secondary antibody Cy3 conjugated goat anti-rabbit IgG (or appropriate secondary antibody for other reagents) in 3% BSA for 1.5 hours. After washing and drying, the slides were scanned on a GenePix scanner (GenePix 4000B Microarray Scanner, Molecular Devices Corporation, Union City, Calif.). The fluorescence was quantified by using GenePix Pro 6.0 software with a GenePix Array List file. The value for each array component was obtained by averaging the background corrected median intensities of the two spots.

Example 5

The methods used for immunohistochemical staining using the antibodies of the present invention are detailed below.

Tissue slides were first heated in a dry oven at about 62° C. in a vertical orientation for 1 hour to remove the wax on the surface. Deparaffinization was completed by further incubating the slides in several changes of xylene for a total of 30 minutes. The slides were then rehydrated in gradual ethanol for a few minutes before immersion in PBS. 0.02% Trypsin PBS solution was used for antigen retrieval by incubating the slides in preheated trypsin solution at 37° C. for 30 minutes. Next, the slides were incubated in a solution of 0.6% hydrogen peroxide ($H_2O_2$) in methanol for 15 minutes, washed with PBS three times, and then incubated for 30 minutes in normal blocking serum to eliminate the nonspecific binding. The slides were then incubated overnight at 4° C. with primary reagent (diluted in 0.1% bovine serum albumin/PBS buffer solution) at their optimized working concentration (132-3=1:15; PolyTn=1:30; 81FR2.2=1:25; DBA=1:500). Slides were washed three times in PBS, incubated with biotinylated secondary reagents at about 7.5 μg/ml concentration (DBA was biotinylated, therefore no secondary reagent was used) for 30 min, and then washed by three changes of PBS. The avidin-biotin complex (ABC) conjugated with horseradish peroxidase (HRP) was then used on the tissue for another 30 minutes. After washing with PBS thoroughly, the slides were developed in 3,3'-diaminobenzidine (DAB) solution for 5 minutes, washed and counterstained with Gill's hematoxylin (Fisher Scientific, Pittsburgh, Pa.) for 6-10 seconds and blued by saturated lithium carbonate solution for 1 minute. The slides were then rinsed with tap water, dehydrated with gradual ethanol, cleared with xylene, and mounted. For negative controls, the primary antibody was replaced by 0.1% BSA/PBS solution (FIGS. 2A-2D).

Example 6

The following paragraph describes the methods used for the pathology grading of tissue sections and the survival analysis method used.

The immunohistochemical staining of tissues was quantified based on staining intensity, location and percentage of the cells stained. The intensities were assigned a rating from 1-4, with 4 representing the most intense staining. Staining locations were indicated as cytoplasm (C), membrane (M), and nucleus (N). The percentage of positive cells was graded using the following five categories: 0=0-10% of cell positively stained; 1=10-24% of cell positively stained; 2=25-49% of cell positively stained; 3=50-74% of cell positively stained; 4=75-100% of cell positively stained. The intensity score and percentage score were combined to yield an overall score. A sample was defined as positive if the overall score was greater than 4. The results were analyzed using Yate's Chi-square test. $P<0.05$ was defined as statistically significant.

Example 7

The immunohistochemical staining of the sample slides and specificity evaluation is detailed below.

GalNAcα1-3Gal is a substructure found within the blood group A antigen and blood group antigens are known to be expressed in a variety of tissues. Antibody 81FR2.2 was used to evaluate blood group A expression, because this antibody has been shown to have good specificity for blood group A in previous studies (Chihara, Y., et al., Lab. Investigation, 85(7): 895-907 (2005)) and on the carbohydrate array. The antibody to GalNAcα1-3Gal and 81FR2.2 showed distinct differences in tissue staining, and GalNAcα1-3Gal antibodies showed no positive staining on a blood group A positive pancreas cancer tissue. Therefore, GalNAcα1-3Gal antibodies do not appear to bind blood group A.

An evaluation of the binding to two tumor-associated carbohydrate antigens that also contain a terminal GalNAc alpha residue (Tn antigen and Forssman antigen), was performed. Expression of the Tn antigen was measured with PolyTn (an affinity purified polyclonal antibody to Tn; (Li, Q., et al., Mol. Cancer. Ther., 8: 971-9 (2009)) and expression of the Forssman antigen was detected with *Dolichos biflorus* agglutinin (DBA) (Hammarström S, et al., Brioche 16(12): 2750-2755 (1977)). Again, staining with antibodies to GalNAcα1-3Gal was different from PolyTn and DBA. Results showed that a kidney tumor sample stained positively for expression of the Tn antigen, while negative staining was observed with antibodies to GalNAcα1-3Gal, indicating that these antibodies do not cross-react to the Tn antigen. Likewise, negative staining by DBA was found on a cervical cancer tissue sample that displayed positive expression of GalNAcα1-3Gal with antibodies from the 132-3 hybridoma. Specific binding of the antibodies of the present invention to GalNAcα1-3Gal was also confirmed using a dot blotting method. The results showed no cross-reactivity of the antibody to BG-A, GalNAcα1-6Gal, the Forssman antigen, or asialo-ovine submaxillary mucin (a protein that expresses high levels of the Tn antigen). Taken together, the results from the microarray, dot blotting, and immunohistochemical staining confirm that antibodies to GalNAcα1-3Gal (including 132-3) specifically recognize the antigen GalNAcα1-3Gal in tissues.

Example 8

The expression of GalNAcα1-3Gal on cervical tissues is discussed in detail below.

The expression pattern of GalNAcα1-3Gal on cervical tissues using antibody 132-3 was investigated. A total of 84 samples were evaluated which included 4 normal tissue, 75 primary tumor samples, and 5 lymph node metastases. The cervical tissue staining results and their correlations to clinical pathological factors are summarized in Table 1. High expression was found on squamous cell carcinomas (55%) and metastatic lymph nodes (100%). On squamous cell carcinomas, strong specific staining was located on the cytoplasm and cell membranes of cancerous cells. Similar patterns could be found on metastatic lymph nodes. Intense staining and clear contrast indicated high expression of GalNAcα1-3Gal on the cancer cells. Most other types of carcinomas, such as adenocarcinomas and small cell carcinomas did not stain well, indicating little or no expression of GalNAcα1-3Gal on these types of tumors. Staining of normal cervical tissue was observed on the suprabasal epithelial layer. There was no correlation between the expression of GalNAcα1-3Gal and a patient's age, tumor size and stage, or if there was lymph node metastasis.

Example 9

In the following paragraph, the correlation of GalNAcα1-3Gal expression and survival in cervical cancer is disclosed.

Survival data was available for 48 of the patients in the study. Positive expression of GalNAcα1-3Gal correlated with increased survival. After 5 years, 18/21 (85%) GalNAcα1-3Gal positive patients were alive whereas only 13/27

Figure 3:
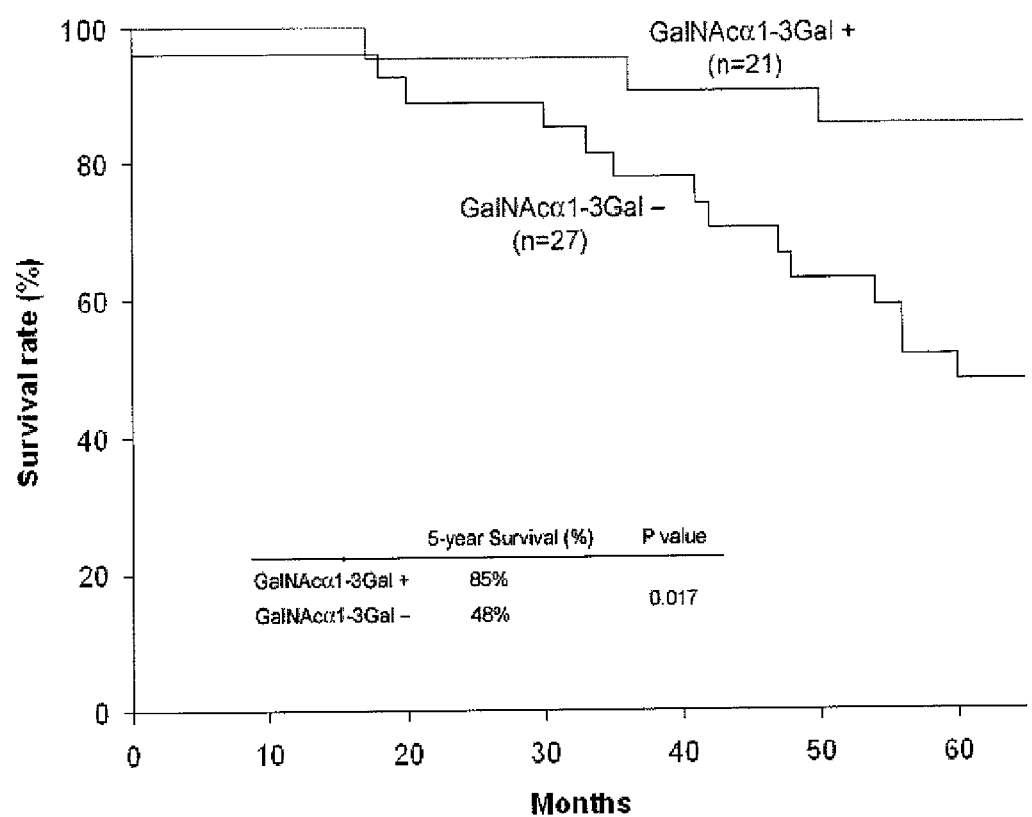
FIG. 3 is a Kaplan Meier 5-year survival curve depicting a survival study according to the expression of GalNAcα1-3Gal antigen in cervical cancer. The inset table shows the p-value calculated using Yate's chi-square test.

(48%) GalNAcα1-3Gal negative patients were alive. The difference in survival was statistically significant (P value=0.017). A Kaplan-Meier curve is shown in FIG. 3. Patients with GalNAcα1-3Gal positive tumors had a substantially higher 5 year survival rate and that the difference between GalNAcα1-3Gal positive and negative patients was statistically significant (P value=0.017). Moreover, expression of GalNAcα1-3Gal did not correlate with other clinical factors, including tumor stage, size and lymph node metastasis, indicating the antigen is an independent biomarker for the prognosis of cervical cancer.

Example 10

The expression pattern of GalNAcα1-3Gal on larynx tissues using antibody 132-3 was investigated.

The larynx cancer tissue microarray slides were purchased from Imgenex Inc. (San Diego, Calif.). Twenty five individual larynx cancer tissues were from Capital Bioscience Inc. (Gaithersburg, Md.). All tissues were classified using TMN system, histotype and stage grading according to the World Health Organization criteria. The methods for the immunohistochemical staining and grading used were the same as discussed in Examples 5 and 6.

Figure 4:
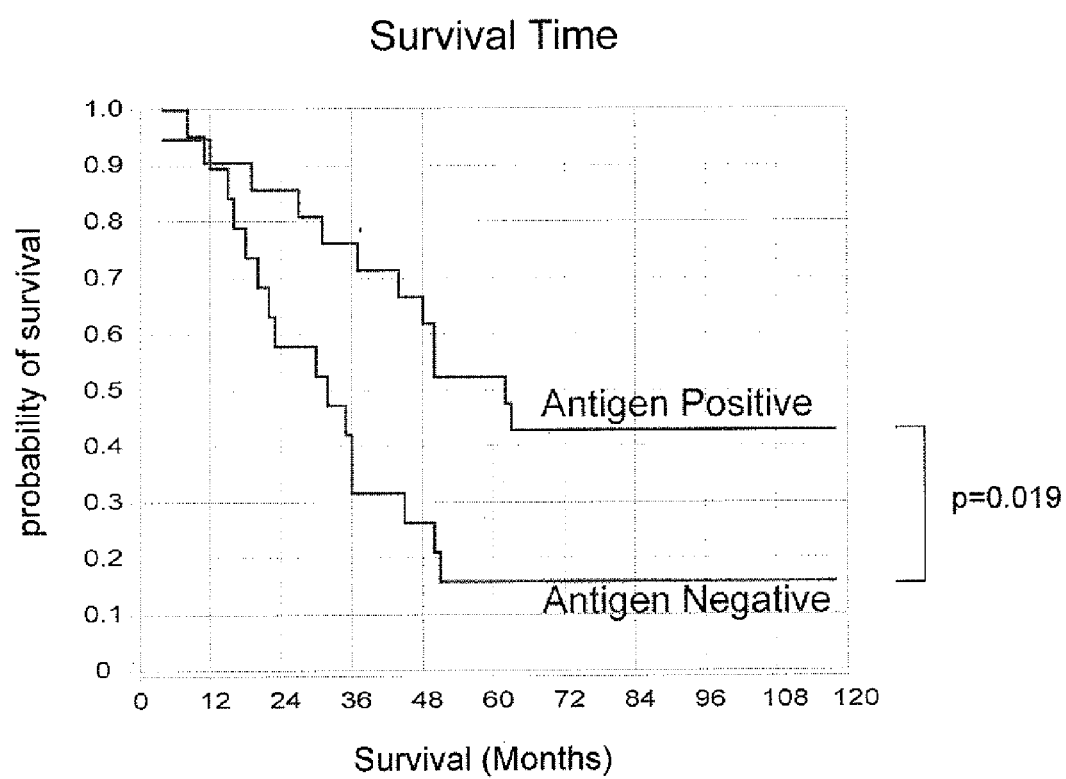
FIG. 4 is a Kaplan Meier 5-year survival curve depicting a survival study according to the expression of GalNAcα1-3Gal antigen in laryngeal cancer. Antigen expression has a statistically significant correlation with positive survival in stage II-IV cancers of the larynx (p=0.0191).

The antibody 132-3 was used to evaluate GalNAcα1-3Gal antigen expression in a various tumor and normal tissues, including larynx tissue. The antigen has intermediate expression in a wide range of tumors, with the most intense and distinct staining of squamous cell carcinomas of the cervix, larynx, and skin (data not shown). There is some expression in normal tissue, but it is fairly restricted. A Kaplan-Meier curve is shown in FIG. 4. Patients with GalNAcα1-3Gal positive larynx tumors had a substantially higher 5 year survival rate. It was found that GalNAcα1-3Gal antigen expression has a statistically significant correlation with positive survival in stage II-IV larynx cancers (p=0.0191; see FIG. 4). Thus the monoclonal antibodies of the present invention can be used as a prognostic marker for larynx cancer.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A monoclonal antibody, or binding fragment thereof, which binds specifically to GalNAcα1-3Gal expressed on the surface of a cancer cell and does not bind to any one or more of blood group A, Tn antigen, GalNAcα1-6Gal, and Forssman antigen.

2. A hybridoma cell line which produces a monoclonal antibody which binds specifically to GalNAcα1-3Gal expressed on the surface of a cancer cell and does not bind to any one or more of blood group A, Tn antigen, GalNAcα1-6Gal, and Forssman antigen.

3. The monoclonal antibody, or binding fragment thereof, according to claim 1, labeled with a detectable moiety.

4. The monoclonal antibody, or binding fragment thereof, according to claim 3, wherein the detectable moiety is selected from the group consisting of a fluorophore, a chromophore, a radionuclide, a chemiluminescent agent, a bioluminescent agent and an enzyme.

5. The monoclonal antibody, or binding fragment thereof, according to claim 1, bound to a solid matrix.

6. A pharmaceutical composition comprising the monoclonal antibody, or binding fragment thereof, according to claim 1, and a pharmaceutically acceptable carrier, excipient, or diluent.

7. A pharmaceutical composition comprising the monoclonal antibody, or binding fragnent thereof, of claim 1, and a therapeutic agent.

8. The pharmaceutical composition according to claim 7 wherein said therapeutic agent is selected from the group consisting of: drugs, radioisotopes, immunomodulators, lectins, toxins, and combinations thereof.

9. The monoclonal antibody, or binding fragment thereof, of claim 1 which does not bind to blood group A.

10. The monoclonal antibody, or binding fragment thereof, of claim 1 which does not bind to Tn antigen.

11. The monoclonal antibody, or binding fragment thereof, of claim 1 which does not bind to GalNAcα1-6Gal.

12. The monoclonal antibody of claim 1, or binding fragment thereof, which does not bind to Forssman antigen.

13. The hybridoma cell line of claim 2 which produces a monoclonal antibody which does not bind to blood group A.

14. The hybridoma cell line of claim 2 which produces a monoclonal antibody which does not bind to Tn antigen.

15. The hybridoma cell line of claim 2 which produces a monoclonal antibody which does not bind to GalNAcα1-6Gal.

16. The hybridoma cell line of claim 2 which produces a monoclonal antibody which does not bind to Forssman antigen.

17. The monoclonal antibody, or binding fragment thereof, of claim 1 which does not bind to any of blood group A, Tn antigen, GalNAcα1-6Gal, and Forssman antigen.

18. The hybridoma cell line of claim 2 which produces a monoclonal antibody which does not bind to any of blood group A, Tn antigen, GalNAcα1-6Gal, and Forssman antigen.

19. The monoclonal antibody, or binding fragment thereof, of claim 1. wherein the cancer cell is a cervical cancer cell.

20. The hybridoma cell line of claim 2, wherein the cancer cell is a cervical cancer cell.

* * * * *